United States Patent
Bozorgi-Ram

Patent Number: 5,661,270
Date of Patent: Aug. 26, 1997

[54] SOUND CAPTURING DEVICE

[76] Inventor: Abbas Bozorgi-Ram, 825 S. Goldenwest Ave. #7, Arcadia, Calif. 91007

[21] Appl. No.: 518,998

[22] Filed: Aug. 24, 1995

[51] Int. Cl.$^6$ .................................. H04R 25/00
[52] U.S. Cl. ........................... 181/129; 181/136
[58] Field of Search .................... 181/129, 130, 181/136, 135; 381/183, 187

[56] References Cited

U.S. PATENT DOCUMENTS

| | | | |
|---|---|---|---|
| 1,708,257 | 4/1929 | Campbell | 181/136 |
| 2,537,201 | 1/1951 | Amfitheatrof | 181/129 |
| 2,844,820 | 7/1958 | Austin et al. | |
| 3,178,723 | 4/1965 | Aileo. | |
| 3,335,720 | 8/1967 | Aileo. | |
| 3,408,658 | 11/1968 | Beguin et al. | |
| 3,661,225 | 5/1972 | Anderson. | |
| 3,796,855 | 3/1974 | Brown et al. | |
| 3,938,616 | 2/1976 | Brownfield | 181/136 |
| 4,529,057 | 7/1985 | Telford. | |
| 4,574,912 | 3/1986 | Fuss et al. | 181/129 |
| 4,620,068 | 10/1986 | Wieder. | |
| 5,332,871 | 7/1994 | Carrigan | 181/135 |

*Primary Examiner*—Khanh Dang
*Attorney, Agent, or Firm*—Michael Zarrabian, Esq.

[57] ABSTRACT

A sound capturing device for directionally capturing sound waves, comprising a shell for encompassing an ear of a wearer, the shell having a front portion and a back portion corresponding to the front and the back of the wearer, respectively. The shell includes at least one opening in the front portion of the shell, the opening sized and positioned to capture sound waves transmitted from a sound source substantially in a pre-selected direction, wherein the wearer perceives said sound source to be located within the shell proximate the ear of the wearer, with reduced interference from other sources of sound not located substantially in the pre-selected direction. Preferably, the device further comprises adjustment means attached to the shell for selectively adjusting the size of the opening to regulate the amount of sound waves entering the opening from the surrounding environment.

18 Claims, 2 Drawing Sheets

SOUND CAPTURING DEVICE

BACKGROUND

The present invention generally relates to sound capturing devices and, in particular, to sound capturing devices for directionally capturing sound waves.

Earphones are used by many individuals to listen to voice or music generated by speakers within the earphones at close proximity to an individual's ears. The proximity of the speakers to the ears is desirable because the generated sound generally dominates other sources of sound in the surrounding environment, thereby providing for listening to voice or music with reduced interference from other sources of sound. The speakers in the earphones are electrically coupled to a sound generation device such as a stereo system.

A disadvantage of existing earphones, however, is that a user must either remain stationary near the sound equipment coupled to the speakers in the earphone or carry the sound equipment with him or her. A further disadvantage is that, although the proximity of the speakers to the ear in existing headphones provides for listening to music or voice generated proximate the ear of the user, in many instances, a user may wish to hear sounds from the surrounding environment such as a door bell, alarm, etc. Because current headphones seal or dominate sounds from surrounding environment, a user usually is cut off from his or her surroundings.

Yet another disadvantage of existing earphones is that a user cannot utilize the earphones for listening to voice or music at close range in locations such as concerts or movie theaters because the user does not have access to the source of sound for coupling the earphones to such source. As such, a user cannot benefit from the desirable sensation of hearing voice or music proximate to his or her ear, even though the source of sound is distant from the user.

There is therefore a need for a device for listening to voice or music wherein the device provides a sound effect comparable to an earphone where the source of sound appears to be proximate to the ear without use of speakers in the device. There is also a need for such a device to be devoid of any need for coupling the device to either a portable or a stationary source of sound. There is also a need for such a device not to seal or dominate sounds from the surrounding environment.

SUMMARY

The present invention satisfies these needs. The invention provides a sound capturing device for directionally capturing sound waves. The device comprises a shell for encompassing an ear of a wearer, the shell having a front portion and a back portion corresponding to the front and the back of the wearer, respectively. The shell includes at least one opening in the front portion of the shell. The opening is sized and positioned to capture sound waves transmitted from a sound source substantially in a pre-selected direction, wherein the wearer perceives the sound source to be located within the shell proximate the ear of the wearer with reduced interference from other sources of sound not located substantially in the pre-selected direction.

The device can further comprise adjustment means attached to the shell for selectively adjusting the size of the opening to regulate the amount of sound waves entering the opening from the surrounding environment. Preferably, the adjustment means comprises a door slidably disposed in the shell, wherein the door can incrementally slide from a first position, where the opening is completely blocked, to a second position, where the opening is not blocked.

Preferably, the shell comprises a cup-like housing for encompassing an ear of the wearer. The shell can be of substantially rigid material. The shell can also be of sound resistant material.

DRAWINGS

These and other features, aspects, and advantages of the present invention will become better understood with reference to the following description, appended claims, and accompanying drawing where:

DESCRIPTION

The following discussion describes in detail one embodiment of the invention and several variations on that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 1:
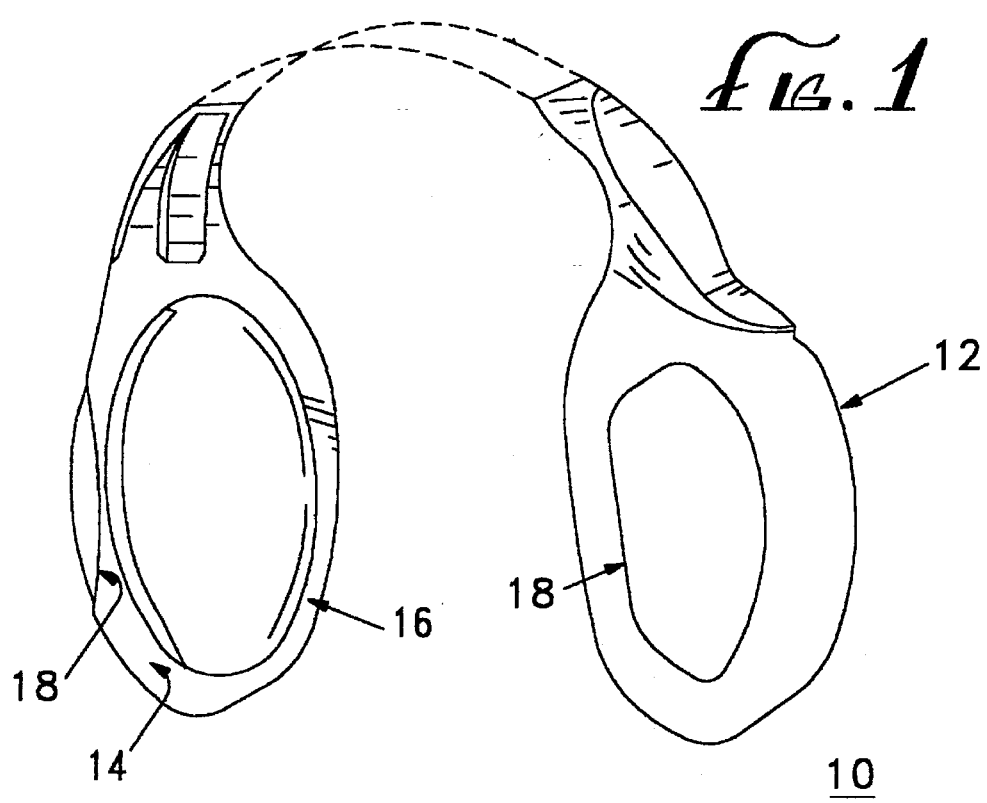
FIG. 1 is a perspective view of an embodiment of the sound-capturing device of the present invention.

Referring to FIG. 1, an embodiment of the present invention is shown. The invention provides a sound capturing device 10 for directionally capturing sound waves. The device 10 comprises a shell 12 for encompassing an ear of a wearer, the shell 12 having a front portion 14 and a back portion 16 corresponding to the front and the back of the wearer, respectively. The shell 12 includes at least one opening 18 in the front portion 14 of the shell 12, wherein the opening 18 is sized and positioned to capture sound waves transmitted from a sound source substantially in a pre-selected direction. As such, the wearer perceives the sound source to be located within the shell 12 proximate the ear of the wearer with reduced interference from other sources of sound not located substantially in the pre-selected direction.

Preferably, the pre-selected direction is forward of the wearer, wherein the wearer perceives a sound source located substantially forward of the wearer to be within the shell 12 proximate the ear of the wearer with reduced interference from other sources of sound not substantially forward of the wearer.

Preferably, the shell 12 is of a substantially rigid material such as plastics. The shell 12 can also be of a semi-flexible material such as styrene.

As shown in FIG. 1, the shell 12 comprises a cup-like housing for encompassing an ear of the wearer, and preferably has only one opening 18 in the front portion of the shell 12 where the opening is elongated.

Figure 2:
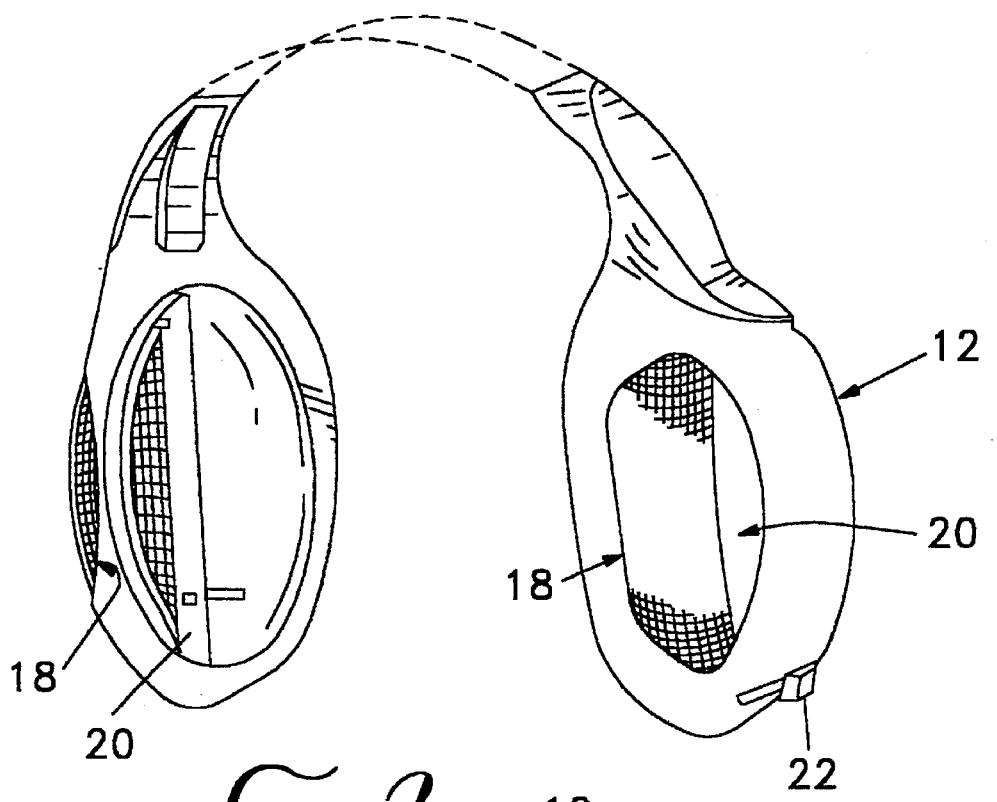
FIG. 2 is a perspective view of another embodiment of the sound-capturing device of the present invention.

As shown in FIG. 2, the device 10 can further comprise an adjustment means 20 attached to the shell 12 for selectively adjusting the size of the opening 18 to regulate the amount of sound waves entering the opening 18 from the surrounding environment. The adjustment means 20 allows incremental adjustment of the size of the opening 18 from a fully open position, to a partially open position, and to a closed position.

Preferably, the adjustment means 20 comprises a door 20 slidably disposed in the shell 12, wherein the door 20 can incrementally slide from a first position where the opening 18 is completely blocked, to a second position where the opening 18 is not blocked. The door 20 can also slide to a partially open position wherein the opening 18 is only partially blocked. If desired, the shell 12 and the door 20 can be of sound resistant material whereby sound waves from the surrounding environment are prevented from entering the shell 12 when the door 20 is closed.

As shown in FIG. 2, a lever 22 is attached to the door 20 to allow a user to manipulate the position of the door 20 to select a desirable attenuation of sound waves entering the opening 18 by adjusting the size of the opening 18 by sliding the door 20 from a fully-opened position, to a partially-opened position, to a closed position, as desired.

The device can further comprise a transducer means attached to the shell 12 for converting electrical signals to audio signals, and means for coupling the audio signals to the wearer's ear. The transducer means and the coupling means can be a speaker, as is known to those skilled in the art. As such, a user of the device can listen to a source of sound generated by the speaker proximate to the ear of the user, in addition to sources of sound external to the device, as described above. The speaker can be electronically coupled to musical equipment such as a stereo system.

The present invention also contemplates a device for capturing sound waves, comprising a shell for encompassing an ear of a wearer, the shell including at least one opening in the shell, the opening sized and positioned to capture sound waves of substantially only a preselected frequency.

The present invention also contemplates a shell made from cardboard or other disposable material whereby a user can utilize the sound capturing device for a limited period of time and then dispose of it. The present invention also contemplates utilizing one shell on a headband to cover only one ear.

Although the present invention has been described with reference to certain preferred versions, many other versions should be apparent to those skilled in the art. Therefore, the spirit and scope of the appended claims should not be limited to the description of the preferred versions contained herein.

EXAMPLE

Figure 3:
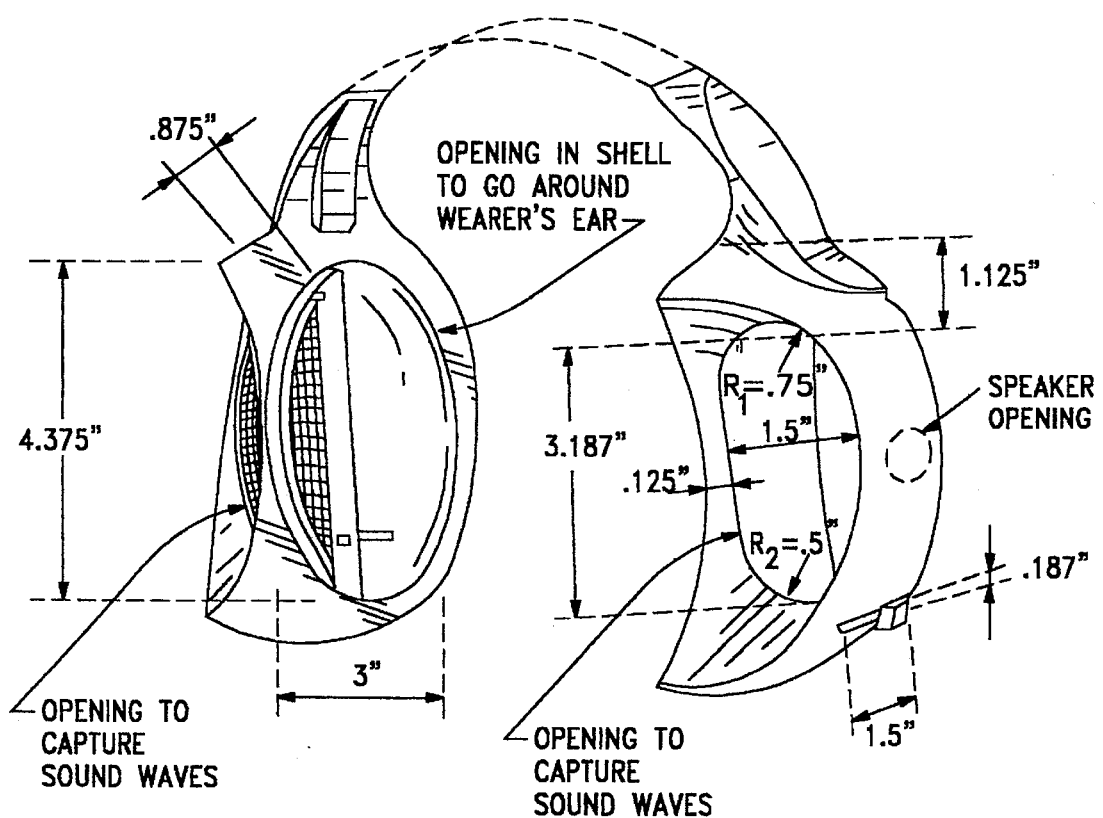
FIG. 3 is a perspective view of an example embodiment of the sound-capturing device of the present invention.

An illustrative example of an embodiment of the sound capturing device of the present invention is shown in FIG. 3. The device comprises a headset having a pair of cup-like shells attached to a headband, as shown. The cup opening of each cup-like shell goes around the ear of a wearer and allows the shell to encompass the ear of the wearer.

Each shell has a front portion and a back portion corresponding to the front and the back of a wearer, respectively. Each shell includes one opening in the front portion of the shell, wherein the opening is sized and positioned to capture sound waves transmitted from a sound source substantially forward of the wearer. As such, the wearer perceives the sound source to be located within the shell proximate the ear of the wearer with reduced interference from other sources of sound not substantially forward of the wearer.

Each shell is elliptical in shape and encompasses an ear of the wearer. As shown in FIG. 3., the dimensions of the shell are about 3" wide, 4⅜" long and 1¾" deep. As shown in FIG. 3, the opening in the shell is elongated substantially in the form of an ellipse and is dimensioned about 1½" wide and 3 3/16" long with a first radius $R_1$ of ¾" and a second radius $R_2$ of ½". The opening is spaced about ⅛" from the rim of the shell as shown. The shell is made of substantially rigid material such as plastics.

The device further comprises a pair of doors, each door slidably disposed in a corresponding shell for adjusting the size of the opening to regulate the amount of sound waves entering the opening from the surrounding environment. The door is concave and elliptical in shape and is made of a material such as plastics. The door is dimensioned to be at least about the size of the opening. Each shell also includes a guide slot in the shell, through which a lever is attached to the door. As such, a user can slide the lever in the slot in order to slide the door to adjust the size of the opening. The slot is dimensioned about 1.5" in length and 3/16" in width. The slot can be formed at any desired location in the shell, and preferably on the lower portion of the front portion of the shell as shown in FIG. 3.

As shown in FIG. 3, each shell can further comprise a sound speaker opening in the shell to allow coupling of a speaker to the shell for generating audio signals from sound equipment such as a stereo system. The opening can have a door for closing the opening when a speaker is not coupled to the shell.

The above discussion of the sound-capturing device of the present invention shown in FIG. 3 is one possible embodiment of the device of the present invention. It is to be understood that the invention is not limited to the device shown in FIG. 3, and that one skilled in the art would readily understand how to modify the disclosed device to obtain equivalent results without departing from the spirit and scope of the present invention.

What is claimed is:

1. A sound capturing device for directionally capturing sound waves, comprising:
    (a) a shell for encompassing an ear of a wearer, the shell having a front portion and a back portion corresponding to a front and a back of the wearer, respectively, the shell including at least one opening in the front portion of the shell, the opening sized and positioned to capture sound waves transmitted from a sound source in a preselected direction from among one or more sound sources located in different directions in a surrounding environment around the wearer, with reduced interference from sources of sound not located in the preselected direction;
    (b) adjustment means attached to the shell for selectively adjusting the size of the opening to regulate the amount of sound waves entering the opening from the surrounding environment, wherein the adjustment means comprises a door slidably disposed in the shell wherein the door can slide from a first position where the opening is completely blocked to a second position where the opening is not blocked.

2. The device of claim 1 wherein the shell is of a substantially rigid material.

3. The device of claim 1 wherein the shell is of a semi-flexible material.

4. The device of claim 1 wherein the shell is of a sound resistant material.

5. The device of claim 1 wherein the opening is elongated.

6. The device of claim 1 wherein the shell has only one opening.

7. The device of claim 1 further comprising transducer means attached to the shell for converting electrical signals to audio signals proximate to the wearer's ear, whereby the wearer can listen to the sound generated by the transducer means and the sound from said sound source in the preselected direction.

8. The device of claim 1 wherein the preselected direction is forward of the wearer.

9. The device of claim 1 wherein the shell comprises a cup-like housing for encompassing an ear of the wearer.

10. The device of claim 1 wherein the adjustment means allows adjustment of the size of the opening from a fully open position, to a partially open position, and to a closed position.

11. A sound capturing device for directionally capturing sound waves, comprising:

(a) a shell for encompassing an ear of a wearer, the shell being of a substantially rigid material and having a front portion and a back portion corresponding to a front and a back of the wearer, respectively, the shell including at least one opening in the front portion of the shell, the opening sized and positioned to capture sound waves transmitted from a sound source forward of the wearer from among one or more sound sources located in different directions in a surrounding environment around the wearer, with reduced interference from sources of sound not located forward of the wearer; and (b) adjustment means comprising a door slidably disposed in the shell for selectively adjusting the size of the opening to regulate the amount of sound waves entering the opening from the surrounding environment.

12. The device of claim 11 wherein the shell comprises a cup-like housing for encompassing an ear of the wearer.

13. A sound capturing device for directionally capturing sound waves, comprising:

(a) a pair of shells for encompassing ears of a wearer, each shell having a front portion and a back portion corresponding to a front and a back of the wearer, respectively, each shell including at least one opening in the front portion of the shell, the opening sized and positioned to capture sound waves transmitted from a sound source in a preselected direction from among one or more sound sources located in different directions in a surrounding environment around the wearer, with reduced interference from sources of sound not located in the preselected direction; and (b) a pair of adjustment means, each attached to a shell and comprising a door slidably disposed in the respective shell for selectively adjusting the size of the opening in the shell to regulate the amount of sound waves entering the opening from the surrounding environment.

14. The device of claim 13 wherein each shell comprises a cup-like housing for encompassing an ear of the wearer.

15. The device of claim 14 wherein the shell comprises of a substantially rigid material.

16. The device of claim 13 wherein the adjustment means comprises a door slidably disposed in the shell wherein the door can slide from a first position where the opening is completely blocked to a second position where the opening is not blocked.

17. The device of claim 13 wherein the opening is elongated.

18. The device of claim 13 wherein the preselected direction is forward of the wearer.

* * * * *